United States Patent [19]

Marlar

[11] Patent Number: 5,016,650
[45] Date of Patent: May 21, 1991

[54] ARM RESTRAINT DEVICE FOR CHILDREN AFFLICTED WITH A COMPULSIVE BITING DISORDER

[76] Inventor: Brian A. Marlar, 23727 Tuscany, East Detroit, Mich. 48021

[21] Appl. No.: 500,006

[22] Filed: Mar. 27, 1990

[51] Int. Cl.⁵ .............................................. A61F 5/37
[52] U.S. Cl. .................................. 128/878; 128/879; 128/880; 128/869; 128/846
[58] Field of Search ............... 128/846, 869, 878, 879, 128/880, 870

[56] References Cited

U.S. PATENT DOCUMENTS

| | | | |
|---|---|---|---|
| 1,636,101 | 7/1927 | McLallen | 128/878 |
| 4,414,969 | 11/1983 | Heyman | 128/878 |
| 4,481,942 | 11/1984 | Duncan | 128/878 |
| 4,745,926 | 5/1988 | Hlusko . | |

Primary Examiner—Robert A. Hafer
Assistant Examiner—Brian E. Hanlon
Attorney, Agent, or Firm—Peter D. Keefe

[57] ABSTRACT

A restraint for disenabling a child afflicted with a compulsive biting syndrome from biting his or her hand or arm, yet otherwise permitting the child substantially free arm movement. The restraint is composed of a brief, two flexible extension members which are each attached to the brief, and a wrist band adjustably connected to each extension members. The object of the structure of the invention is to secure the brief about the waist and groin of the child, then secure each of wrist bands to the arms of the child adjacent the wrists, then adjust the length of the extension members so that the child will be able to move his or her arms in substantial freedom, yet not be able to move his or her arms so that his or her arm may come into contact with the his or her mouth, thereby preventing the child from biting himself or herself.

5 Claims, 1 Drawing Sheet

ARM RESTRAINT DEVICE FOR CHILDREN AFFLICTED WITH A COMPULSIVE BITING DISORDER

BACKGROUND OF THE INVENTION

1. Field of the Invention

The present invention relates to arm restraints for children afflicted with a biting disorder in which the child compulsively bites his or her hands and arms.

2. Description of the Prior Art

Children afflicted with compulsive biting disorders tend to continually bite at various things, such as their arms (inclusive of their hands). This becomes extremely problematical, because wounds frequently result from the compulsive biting, which only exasperate the medical condition.

Applicant is aware of a prior art arm restraint which is presently being marketed in which a sleeve is placed over each arm at the elbow so that the arms of the child cannot be bent. The theory of the device is that if the arms cannot be bent, then they cannot be manipulated to the vicinity of the mouth. While in fact this theory is correct, in practice there is the very extreme draw-back that the child is not permitted to bend his or her arms for extended durations of time. The child may eventually develop neuro-muscular problems from the prevention of natural motor function. These problems can include the eventual loss of normal use of the arms.

Clearly, what is needed in the art is a humane arm restraint that permits arm movement, yet does not permit any portion of the arm to come into contact with the mouth of the child.

SUMMARY OF THE INVENTION

The present invention is an arm restraint for a child afflicted with a biting disorder in which the arms of the child are largely free to move, yet the child will not be able to bring any portion of his or her arms (inclusive of his or her hands) into contact with his or her mouth.

A hour-glass shaped flexible material is releasably fastened around the waist and lower extremities of the child so as to form a brief. The brief includes two flexible extension members which are each attached adjacent the waist area of the brief. Each extension member has connected to it an adjustable wrist band, and each of the extension members is adjustable so as to selectively adjust the maximum distance permissible between its associated wrist band and the brief.

In operation, the brief is secured to the child. Then, successively, each wrist band is fastened around a respective wrist or forearm of the child. The length of each of the extension members is then examined to see whether the child can succeed in moving any portion of his or her arms into mouth contact. If so, then the connection of the wrist band relative to the extension member is adjusted so as to ensure that the desired arm to mouth prohibition is in fact operating.

Accordingly, it is an object of the present invention to provide an arm restraint for a child afflicted with a biting disorder in which the child's arms are able to move in a substantially free manner, except that the child is unable to move his or her arms so that mouth contact can be made with his or her arms, inclusive of his or her hands.

It is a further object of the present invention to provide a cost effective and, more importantly, medically effective, child biting restraint in which the arms of the child are prevented from moving so that he or she may be able to bite any portion of his or her arms, yet the child's neuro-muscular function of his or her arm is substantially retained while the restraint is in operation.

These, and additional objects, advantages, features and benefits of the present invention will become apparent from the following specification.

DETAILED DESCRIPTION OF THE PREFERRED EMBODIMENT

Figure 1:
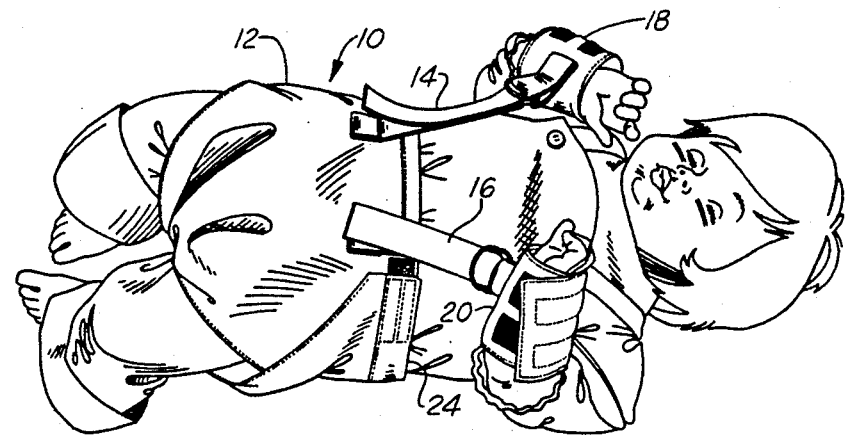
FIG. 1 is a perspective view of the child arm restraint, shown in operation.

Referring now to the Drawing, FIG. 1 shows the restraint 10 according to the present invention in operation. The restraint 10 is composed generally of a brief 12, two extension members 14 and 16 which are attached to the brief 12, and a releasable wrist band 18, 20 connected, respectively, to each of the extension members. The object of the structure of the invention is to secure the brief 12 about the wrist and groin of the child, secure each of wrist bands 18 and 20 to the arms of the child, then adjust the length of the extension members 14 and 16 so that the child will be able to move his or her arms in substantial freedom, yet not be able to move his or her arms so that any portion of his or her arms may come into contact with the child's mouth, thereby preventing the child from biting himself or herself.

Referring now to each of FIGS. 1 through 3 the construction and operation of the present invention will be explained in detail.

The brief 12 is preferred to be constructed of a fabric material, such as cotton. It is preferred that the brief 12 be structured of a flexible material 12a having an hourglass shape (as shown particularly in FIGS. 2 and 3), since this permits the brief to be easily placed on the child in the manner common to diapers. Of course, a brief of a pre-formed pant shape is also within the contemplation of the present invention, but this is less desirable because of the greater difficulty of putting it on and off the child. Returning now to the preferred brief which is structured of a flexible material having hourglass shape, a releasable fastener 22, located along the waist line 24 of the brief 12, is used permit easy releasable interconnection of the upper portion 26 and lower portion 28 of the flexible material 12a, so as to form the brief 12 as shown in FIG. 1. A preferred releasable fastener 22 is VELCRO, a trademark for a hook and loop fastener system made by Velcro, U.S.A.

The extension members 14 and 16 are preferred to be constructed of flexible fabric strips, such as strips of a cotton material. Each extension member is secured at one end 30 to the brief 12 adjacent the waist line 24 by any conventional fastening mechanism, such as sewing 32.

Interconnected with each extension member is, respectively, a wrist band 18, 20. The wrist band is preferred to be constructed of flexible fabric, such as cotton, and dimensioned so that it may loop around a selected portion of the child's arm, preferably the wrist and/or forearm adjacent thereto. The width of the wrist band should be at least wide enough to ensure that the child will not be hurt by pinching should he or she tug on the wrist band in an attempt to bring his or her arm to his or her mouth, yet not so wide as to exceed the length of the child's forearm (thus avoiding unnecessary interference with arm bending at the elbow). A releasable fastener 34 is located at opposite ends 36 and 38 of each wrist band so as to permit easy fastening of the wrist band about the child's wrist and/or forearm. A preferred releasable fastener is, again, the product manufactured under the VELCRO trademark.

Each of the wrist bands 18 and 20 are interconnected with its respective extension member 14, 16 in an adjustable manner, as follows. A loop member 40, 42 is connected, respectively, to each wrist band at a location selected so that it will not interfere with placement of the wrist band on the child's wrist and/or forearm. The loop member 40, 42 is again preferred to be of a flexible fabric composition, such as cotton, and is attached to the wrist band by any suitable fastening mechanism, such as sewing 44. Entrapped in each loop member is a ring 46. Each extension member 18, 20 threads through a ring 46 of a respective wrist band, and is thereupon looped back onto itself using a releasable fastener 48, such as, again, the product manufactured under the VELCRO trademark.

Figures 2, 3:
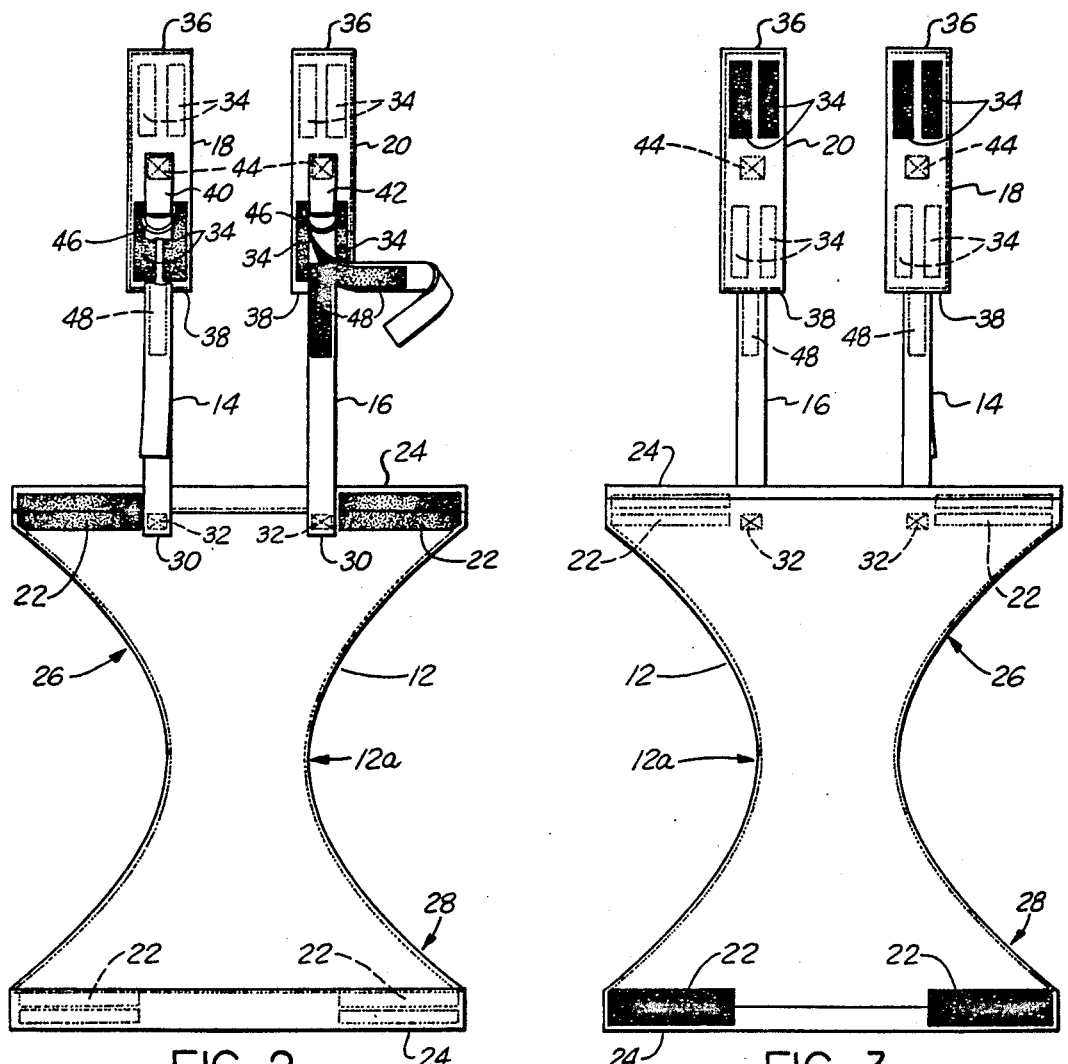
FIG. 2 is a front view of the restraint according to the present invention.
FIG. 3 is a rear view of the restraint according to the present invention.

In operation, the child lays down upon the flexible material 12a while in the flat hour-glass configuration depicted in FIG. 3. The lower portion 28 of the flexible material is then folded toward the upper portion 26 of the flexible material so as to form a brief 12 on the child and the releasable fasteners 22 are thereupon connected together. A wrist band 18, 20 is then secured to each of the child's wrists by looping it about the wrist and/or forearm and then securing it via the releasable fastener 34. Next, an evaluation is made to determine whether the child is able to effect contact between his or her mouth and his or her arm. If so, then one or both extension members should be adjusted. Adjustment is effected by releasing the extension member interconnection at the releasable fastener 48, adjusting the looping of the extension member back on itself to a new spot on the releasable fastener 48 so as to shorten the maximum permissible distance of the respective wrist band from the brief, thereby preventing the child from being enabled to place his or her arms (inclusive of hands) into contact with his or her mouth. It is desired that the ideal distance between the wrist band and the brief be adjusted such so as to permit the child's arms maximum free movement just shy of being able to bring any portion of his or her hands into contact with his or her mouth.

To those skilled in the art to which this invention appertains, the above described preferred embodiment may be subject to change or modification. For instance, while a child has been described herein as the wearer of the restraint 10, it is also intended that the restraint 10 be used by adults. Also, the restraint 10 is further also intended to serve in the capacity of restraining the wearer from hitting/and or injuring his or her head by using his or her arms. Such change or modification can be carried out without departing from the scope of the invention, which is intended to be limited only by the scope of the appended claims.

What is claimed is:

1. A restraint for restraining an individual from making contact between his or her arms and a preselected location upon his or her head, said restraint comprising:

a brief, said brief being structured for placement around the individual's waist and groin, the waist of the individual defining a waist line of said brief;

a first extension member connected to said brief adjacent said waist line, said first extension member being constructed of an inelastic, flexible material;

a second extension member connected to said brief adjacent said waist line, said second extension member being constructed of an inelastic flexible material;

a first wrist band interconnected with said first extension member, said first wrist band being constructed of a flexible material that is structured to wrap around a substantial portion of the forearm of a first arm of said individual between the elbow and the wrist of said first arm, said first wrist band being dimensioned so as to permit the individual to jointably move both the elbow and the wrist of said first arm;

a second wrist band interconnected with said second extension member, said second wrist band being constructed of a flexible material that is structured to wrap around a substantial portion of the forearm of a second arm of said individual between the elbow and the wrist of said second arm, said second wrist band being dimensioned so as to permit the individual to jointably move both the elbow and wrist of said second arm;

first releasable fastener means connected with said first wrist band for releasably securing said first wrist band in a selectively wrapped configuration about the forearm of said first arm of said individual; and second releasable fastener means connected with said second wrist band for releasably securing said second wrist band in a selectively wrapped configuration about the forearm of said second arm of said individual;

wherein said individual is able to move his or her arms in substantial freedom, yet he or she is unable to move his or her arms such as to effect contact between his or hers arms and his or her mouth.

2. The restraint of claim 1, further comprising:

first extension adjustment means connected with said first extension member for adjusting a maximum preselected permissible distance between said first wrist band and said brief; and second extension adjustment means connected with said second extension member for adjusting a maximum preselected permissible distance between said second wrist band and said brief.

3. The restraint of claim 2, wherein said brief is structured of a flexible material having an hour-glass shape; said restraint further comprising a third releasable fastener means connected to said brief adjacent said waist line for enabling said flexible material to be constructed into said brief on said individual.

4. The restraint of claim 3, wherein said first and second extension adjustment means comprise:

a first loop member means interconnected with said first wrist band;

a fourth releasable fastener means located on said first extension member, such that said first extension member may be threaded through said first loop member means and then selectively secured back onto itself at said fourth releasable fastener means so as to define said preselected permissible distance between said brief and said first wrist band;

a second loop member means interconnected with said second wrist band; and, a fifth releasable fastener means located on said second extension member, such that said second extension member may be threaded through said second loop member means and then selectively secured back onto itself at said fifth releasable fastener means so as to define said preselected permissible distance between said brief and said second wrist band.

5. The restraint of claim 4, wherein each of said first, second, third, fourth and fifth releasable fasteners is a hook and loop fastener.

* * * * *